United States Patent [19]

Saville

[11] Plant 5,164

[45] Dec. 27, 1983

[54] NEW ROSE PLANT

[75] Inventor: F. Harmon Saville, Rowley, Mass.

[73] Assignee: Nor'East Miniature Roses, Inc., Rowley, Mass.

[21] Appl. No.: 411,357

[22] Filed: Aug. 25, 1982

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety with high centered yellow orange colored blooms having near white outer petals that quill to star-like points.

1 Drawing Figure

The present invention relates to a new and distinct variety of rose plant of the miniature rose class, which was originated by my crossing as seed parent the rose known as "Rise 'N Shine" (PP 4231) and the rose known as "Sheri Anne" (U.S. Plant Pat. No. 3,826) as pollen parent. The denomination of this rose is "Savasilk".

Among the novel characteristics possessed by this new variety which distinguish it from its parents and all other varieties of which I am aware are high centered, nicely formed blooms of yellow orange coloring and heavy petalage with petals that quill to light colored star-like points as flowers open. Asexual reproduction by budding of the new variety as performed in Essex County, Massachusetts, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "19A" is plate 19A of The Royal Horticultural Society Colour Chart.

Parentage: Seedling.

*Seed parent.*—"Rise 'N Shine".

*Pollen parent.*—"Sheri Anne".

Class: Miniature.

The following observations are made of specimens grown outdoors in Essex County, Massachusetts during the month of June.

1. FLOWER

Blooming habit: Recurrent.

A. Bud:

(1) *Size.*—Medium.

(2) *Form.*—Ovoid, elongated.

(3) *Color.*—After sepals divide, near 19A.

(4) *Sepals.*—Ordinary, slightly longer than bud.

(5) *Peduncle.*—Length — About 1 to $1\frac{1}{4}$ inch. Aspect — Straight. Strength — Erect. Color — Near 144C.

B. Bloom:

(1) *Size.*—Average size when fully expanded — About $1\frac{1}{2}$ to $1\frac{3}{4}$ inches.

(2) *Borne.*—Singly and sprays of usually three blooms.

(3) *Form.*—High centered, outer petals quill to star-like points, inner petals also roll under.

(4) *Petalage.*—Number of petals under normal conditions — About 40 to 45.

(5) *Color.*—As petals unfurl, tonal difference is seen between outer petals which tend to be lighter, 27D and 27C, at the top petal surface and the petal undersurface which tends toward a coloring between 24C and 24D. Where petals bunch, such as flower center in $\frac{1}{3}$ to 178 open stage, tonality is more intense and color appears deeper, lightening in shading to near white at outer petals 27D. Color at point of petal attachment is near 17C. General tonality from a distance is yellow orange at flower center with lighter outer petals which tend to lighten further as flowers age.

C. Petals:

(1) *Texture.*—Thick.

(2) *Appearance.*—Inside and outside satiny.

(3) *Form.*—Fan shaped with sharp apices.

(4) *Arrangement.*—Regularly arranged, shingle-like.

(5) *Petaloids in center.*—Few to many.

(6) *Persistence.*—Drop off cleanly.

(7) *Fragrance.*—Slight.

(8) *Lasting quality.*—Long lasting on plant and as cut flower.

2. REPRODUCTIVE ORGANS

A. Stamens, filaments and anthers:

(1) *Arrangement.*—Stamens regularly arranged around styles.

(2) *Color.*—Near 17A.

B. Pollen:

*Color.*—Near 17A.

C. Styles: Even, medium length, thin.

D. Stigmas:

*Color.*—Near 18C.

E. Hips: None observed.

3. PLANT

A. Form: Upright, compact.

B. Growth: Vigorous, uniform branching.

*Height attained.*— *About* 14 to 16 inches.

C. Foliage: Compound 5 to 7 leaflets.

(1) *Size.*—Medium.

(2) *Quantity.*—Abundant.

(3) *Color.*—New foliage: Upper side — Near to 143A. Under side —Near to 148C. Old foliage: Upper side — Near to 137A. Under side —Near to 139C.

(4) *Shape.*—Oval, pointed.

(5) *Texture.*—Upper side is glossy and under side is matte.

(6) *Edge.*—Serrated.

(7) Serration.—Even.

(8) *Leaf stem.*—Color — Near to 143C. Under side — Near 146C.

(9) *Stipules.*—Long with long points.

(10) *Resistance to disease.*—Blackspot — Average. Mildew — Average. Rust — Average.

D. Wood:

(1) *New wood.*—Color — Near 146C. Bark — Smooth.

(2) *Old Wood.*—Color — Near 43B. Bark — Smooth.

E. Thorns:

(1) *Thorns.*—Quantity (main stalk) — Ordinary. On laterals from stalk — Average. Form — straight, thin. Length — Medium. Position — Scattered.

(2) *Prickles.*—None.

F. Winter hardiness.: Needs protection in severe climate.

I claim:

1. A new and distinct variety of rose plant of the miniature rose class, substantially as shown and described, characterized particularly by heavily petaled, high centered yellow orange blooms with near white outer petals that quill to star-like points.

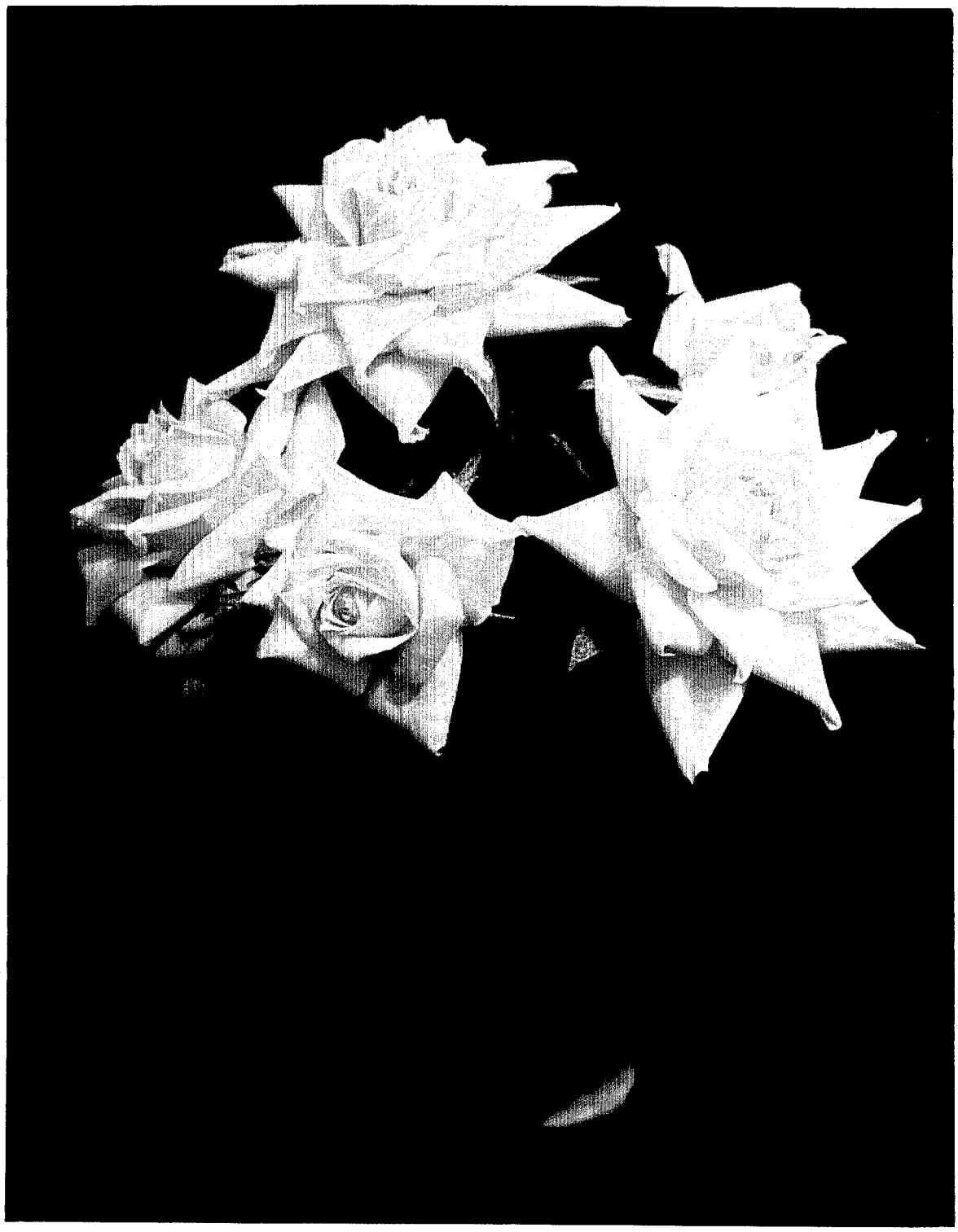

* * * * *